(12) United States Patent
Chen et al.

(10) Patent No.: US 6,383,812 B1
(45) Date of Patent: May 7, 2002

(54) ANTI LIVER DISEASE DRUG R-YEEE AND METHOD OF SYNTHESIZING BRANCHED GALACTOSE-TERMINAL GLYCOPROTEINS

(75) Inventors: Shui-Tein Chen; Weir-Torn Jiaang, both of Taipei; Ping-Hui Tseng, Wur; Chun-Ming Huang, Kaoshiung, all of (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/490,734

(22) Filed: Jan. 25, 2000

Related U.S. Application Data
(60) Provisional application No. 60/136,521, filed on May 28, 1999.

(51) Int. Cl.$^7$ .......................... C12N 15/09; C12N 15/63; C07H 21/04
(52) U.S. Cl. ...................... 435/455; 536/24.5; 530/333; 530/335; 530/395
(58) Field of Search ................................ 530/333, 395, 530/391.9, 391.7; 435/375, 325, 455; 514/2–21

(56) References Cited

U.S. PATENT DOCUMENTS

| | | |
|---|---|---|
| 4,859,449 A | 8/1989 | Mattes |
| 5,346,696 A | 9/1994 | Kim |
| 5,874,297 A | 2/1999 | Wu et al. |

OTHER PUBLICATIONS

Ashwell, G. et al., "Carbohydrate–Specific Receptors of the Liver", *Ann. Rev. Biochem.*, 1982. 51:531–54 (p2, ln.11).

Lee, Reiko T. et al., "Rabbit and Rat Hepatic Lectins Have Two–Sugar–Combining Sites Per Monomeric Unit", *Biochemical and Biophysical Research Communications*, 1988, 155: 1444–1451 (p2, ln.14).

Lee, Y.C., "Biochemistry of Carbohydrate–Protein Interaction", *FASEB*, 1992, 6:3193–3200 (p2, ln.14).

Lee, Reiko T. et al., "Preparation of Cluster Glycosides of N–Acetylgalactosamine That Have Subnanomolar Binding Constants Towards the Mammalian Hepatic Gal/GalNAc–specific Receptor", *Glycoconjugate J.*, 1987, 4:317–328 (p2,ln.16–17).

Merwin, June Rae et al., "Targeted Delivery of DNA Using YEE/(GalNAcAAH)$_3$, A Synthetic Glycopeptide Ligand For the Asialoglycoprotein Receptor", *Bioconjugate Chem.*, 1994, 5:612–620 (p3, ln.5).

Hangeland, Jon J. et al., "Cell–Type Specific and Ligand Specific Enhancement of Cellular Uptake of Oligodeoxynucleoside Methylphosphonates Covalently Linked With a Neoglycopeptide, YEE(ah–GalNAc)$_3$", *Bioconjugate Chem.*, 1995, 5:695–701, (p3,ln.5).

"A New Procedure For The Preparation Of Oligosaccharide Oxazolines;Satoru", Nakabayashi, et al., *Carbohydrate Research*, 150 (1986) pC7–C10.

"Stepwise Synthesis Of A GalNAc–Containing Cluster Glycoside Ligand Of The Asialoglycoprotein Receptor"; Mark A. Findeis; International Journal of Peptide & Protein Research; International Journal of Peptide & Protein Research 43. 1994, 477–485.

"New Synthetic Cluster Ligands For galactos/N–Acetylgalactosamine–Specific Lectin of Mammalian Liver"; Reiko T. Lee, et al.; Biochemistry 1984, 23, 4255–4261.

"Synthesis Of Cluster Galactosides With High Affinity For The Hepatic Asialoglycoprotein Receptor"; Erik A. L. Biessen, et al.; J. Med. Chem. 1995, 38, 1538–1546.

*Primary Examiner*—Sean McGarry
*Assistant Examiner*—Janet L. Epps
(74) *Attorney, Agent, or Firm*—Cohen, Pontani, Lieberman & Pavane

(57) ABSTRACT

The present invention provides a novel method of synthesizing branched galactose-terminal glycoproteins. A number of these glycoproteins have binding affinity to the asialoglycoprotein receptor. The present invention also provides novel conjugates having branched galactose-terminal glycoproteins that is complexed to a therapeutically effective agent, such as an isolated protein, polysacharides, lipids and radioactive isotope. These conjugates may be used to deliver the therapeutically effective agent to mammalian cells generally, and to hepatocytes specifically.

30 Claims, No Drawings

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Tyr Glu Glu Glu
 1

```
<210> SEQ ID NO 2
<211> LENGTH: 20
<212> TYPE: DNA
<213> ORGANISM: Artificial Sequence
<220> FEATURE:
<223> OTHER INFORMATION: Description of Artificial  Sequence: Synthetic
      oligonucleotide

<400> SEQUENCE: 2
cagccatggt tcccccaac                                                    20
```

ANTI LIVER DISEASE DRUG R-YEEE AND METHOD OF SYNTHESIZING BRANCHED GALACTOSE-TERMINAL GLYCOPROTEINS

RELATED APPLICATIONS

The present application claims benefit under 35 USC 119(e) of provisional application, Ser. No. 60/136,521, filed May 28, 1999, the contents of which is fully incorporated by reference.

BACKGROUND OF THE INVENTION

1. Field of the Invention

The present invention relates to a novel method of synthesizing ligands for the asialoglycoprotein receptor, a recycling endocytotic receptor on the surface of mammalian hepatocytes. Novel ligands having affinity to the asialoglycoprotein receptor and a method of synthesizing thereof are also disclosed.

2. Description of the Related Art

Mammalian liver cells possess specific membrane-bound receptors, asialoglycoprotein receptors (ASGPr), which receive ligands having terminal galactose/N-acetylgalactosamine residues. Ashwell el al., *Annu. Rev. Biochem.*, 1982, 51, 531. The affinity of such a receptor to its ligand depends on the valency of the terminal galactose (Gal) or N-acetylgalactosamine (GalNAc), Lee et al., *Biochem, Biophys. Res. Commun.*, 1988, 155, 1444, as well as on the three-dimensional arrangement of the sugar residues. Lee, *FASEB*. 1992, 6, 3193–3200.

Lee et al. reported a synthetic ASGPr ligand, YEE(GalNAcAH)$_3$, having a GalNAc-containing trivalents and an affinity of subnanomolar to the ASGP-r. *Glycoconjugate J.*, 1987, 4, 317–328. YEE(GalNAcAH)$_3$ has the following structure:

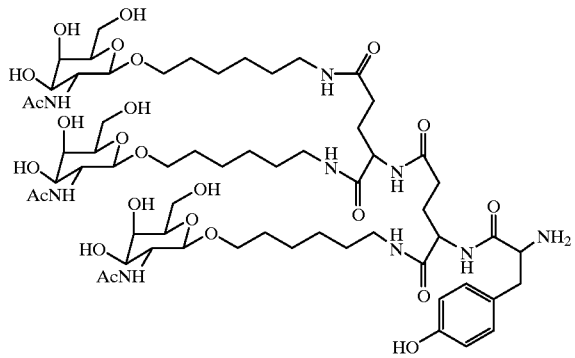

The use of YEE(GalNAcAH)$_3$ as a vehicle for delivery of a gene or an antisense oligodeoxynucleotide to the liver has been also reported recently. Merwin et al. *Bioconjugate Chem.* 1994, 5, 612–620; Hangeland et al., *Bioconjugate Chem.* 1995, 5, 695–701. However, synthesis of YEE(GalNAcAH)$_3$ suffers from some practical problems mainly due to the poor solubility of its peptide intermediates in either aqueous or organic solvents.

Therefore, it is desirable to develop a method of synthesizing YEE(GalNAcAH)$_3$ devoid of the solubility problems encountered by others.

SUMMARY OF THE INVENTION

Accordingly, an object of the present invention is directed to a novel process for synthesizing a general class of branched glycoside ligands having binding affinity to asialoglycoprotein receptor, and potentially useful for specific drug delivery to the liver.

Another object of the present invention is directed to a novel process for synthesizing YEE(GalNAcAH)$_3$ using protected GalNAc derivatives as building blocks through a stepwise solid-phase peptide synthesis (SPPS) technique. The present process of synthesizing YEE(GalNAcAH)$_3$ is simpler, more efficient and economical than the conventional processes and devoid of the problems of the conventional methods.

Another object of the present invention is directed to the synthesis of novel ligands of asialoglycoprotein receptors, for example YEEE(GalNAcAH)$_3$, which is an analog of YEE(GalNAcAH)$_3$, synthesized by a process similar to the synthesis of YEE(GalNAcAH)$_3$. The analog maintains affinity to asialoglycoprotein receptors comparable to YEE(GalNAcAH)$_3$. YEEE(GalNAcAH)$_3$ has the following structure:

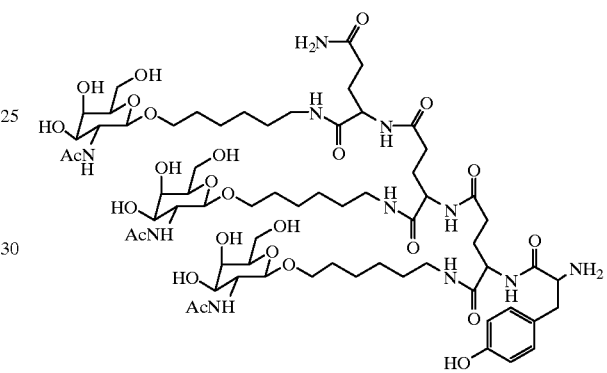

Another object of the present invention is directed to the general class of branched glycoside ligands having binding affinity to asialoglycoprotein receptor (including YEE(GalNAcAH)$_3$ and YEEE(GalNAcAH)$_3$), wherein the ligands are complexed to a therapeutically effective agent. Such therapeutically effective agents include nucleic acids, proteins, polysaccharides, lipids and radioactive isotopes. Preferred nucleic acids include DNA or RNA. A preferred protein is interferon. Such branched glycoside ligands complexed to a therapeutically effective agent may be used to transfect hepatocytes. An especially preferred complex for transfecting hepatocytes is a complex comprising YEEE(GalNAcAH)$_3$ and a group consisting of sequences of antisense oligonucleotides of PKC. (protein kinase C) α: sequence (5'-3') CAGCCATGGTTCCCCCCAAC. (SEQ ID NO: 2).

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENT

Abbreviations

YEE(GalNAcAH)$_3$: tris-(N-acetylgalactosamine aminohexyl)glycoside of tyrosyl(glutamyl)glutamate.

YEEE(GalNAcAH)₃: tris-(N-acetylgalactosamine aminohexyl)glycoside of tyrosyl(glutamyl)₂ glutamate.

YEE: tyrosyl (γ-glutamyl)glutamate

YEEE: tyrosyl (γ-glutamyl)₂ glutamate (SEQ ID NO: 1)

GalNAcAH: 1-(6-aminohexyl)-2-deoxy-D-galactopryranose

ASGPr: asialoglycoprotein receptor

Ac: acetyl

AH: aminohexyl

Bn: benzyl

Bu: butyl

DCC: dicyclohexylcarbodiimide

DMAP: 4-dirnethylaminopyridine

DMF: dimnethylformamide

Et: ethyl

EA: ethyl alcohol

Fmoc: 9-fluorenylmethyloxycarbonyl

Me: methyl

PyBOP: benzotriaole-1-yl-oxy-tris-pyrrolidino-phosphonium hexafluorophosphate

TEA: triethylamine

TFA: trifluoroacetic acid

THF: tetrahydrofiran

The synthesis of YEE(GalNAcAH)₃ and YEEE (GalNAcAH)₃ is as follows.

Scheme 1 and scheme 2 show the procedures to synthesize the starting materials. Scheme 3 shows the procedure for synthesizing YEE with the solid phase method. And scheme 4 shows the procedure for synthesizing YEEE (SEQ ID NO: 1) with the solid phase method.

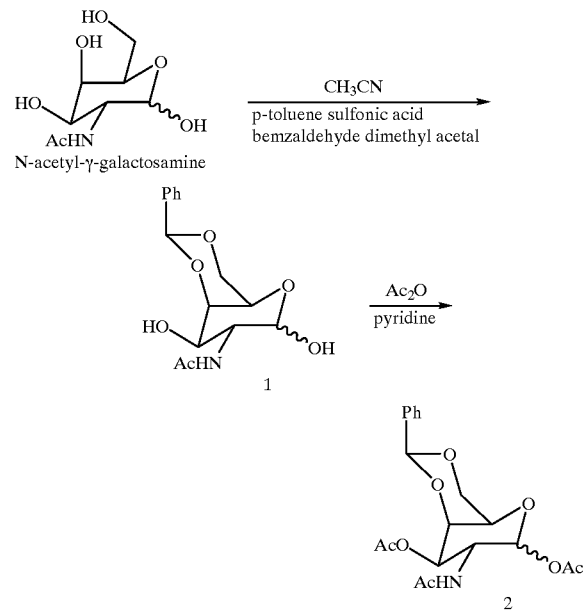

N-acetyl-γ-galactosamnine (SIGMA, MW: 221, 22.1 g, 100mmole) was suspended in dry acetonitrile (LAB-SCAN, 300 mL), p-Toluene sulfonic acid (Lancaster, MW: 190.22, 0.76 g, 5 mmole) and benzaldehyde dimethyl acetal (ACROS, MW: 152.19, d: 1.01, 30.1 mL, 200 mmole) were added. The resulting solution was stirred at room temperature under N₂ for overnight. The mixture was neutralized with Et₃N, and then the crude product was concentrated in vacuo (water pump). Ether was added and filtered, and then the precipitate 1 (MW: 309) was washed by cool water and dried in vacuo (oil pump).

The white solid 1 (benzylidine protected product) was dissolved in pyridine (ACROS, 200 mL), and then Ac₂O (ACROS, MW: 102.09, d: 1.087, 28.2 mL, 300 mmole) was added. The resulting mixture was stirred at room temperature for 4 hr., and the excess Ac₂O and pyridine was removed in vacuo (Rotavapor connected to oil pump). The residue was added ether, and filtered. The precipitate was dried in vacuo (oil pump) to give a white solid 2 (MW: 393, 31.8 g) with 81% yield.

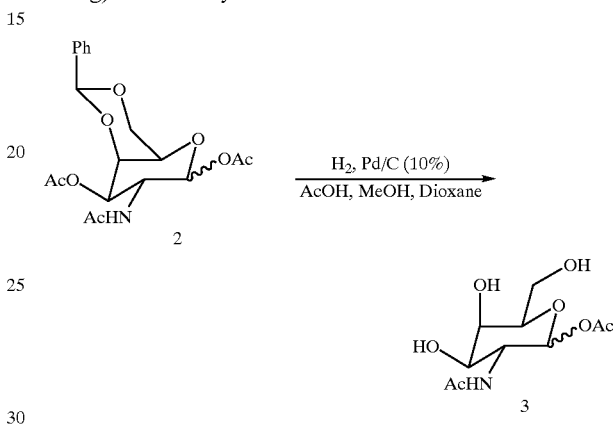

A solution of 2 (3.93 g, 10 mmole) in AcOH/MeOH/Dioxane (1:1:1, 300 mL) was shaken at a hydrogen pressure of 4 bar in the presence of palladium on carbon (10% Pd) (Lancaster, 5 g) at room temperature for 36 hr. The residue was filtered through celite and 2 washed with methanol. The combined filtrates were concentrated in vacuo (water pump) to give a white solid 3 (MW: 305).

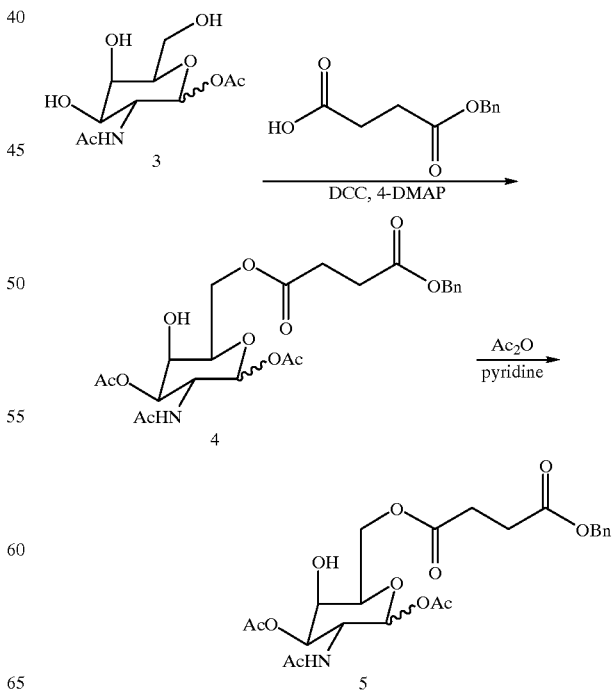

To a solution of 3 (3.05 g, 10 mmole), succinic acid monobenzyl ester (MW: 208, 2.08 g, 10 mmole) in dry THF (40 mL) under $N_2$ and DCC (P peptide institute, MW: 206, 2.68 g, 13 mmole) in dry THF (10 ML) were added at 0° C. The resulting solution was stirred at room temperature for 30 min, followed by added 4-DMAP (MERCK, MW: 122.17, 61mg, 0.5 mmole) and stirred at 0° C. for 2 hr. The mixture was diluted with ethyl acetate (200 mL) and filtered. The filtrate was washed with sat. $NaHCO_3$ solution (100 mL), sat. NaCl solution (100 mL), and then the organic layer was dried ($MgSO_4$), concentrated in vacuo (water pump) to give 4 (MW: 495).

The crude 4 was dissolved in pyridine (50 mL) and $Ac_2O$ (1.88 mL, 20 mmole), and stirred at room temperature for 2 hr. The resulting solution was concentrated in vacuo (Rotavapor connected to oil pump), and the residue was purified by flash chromatography [$EA/CH_2Cl_2$ (1: 1.6)] to give 5 (MW: 537, 3.56 g) with 66% yield from 3 as a foam.

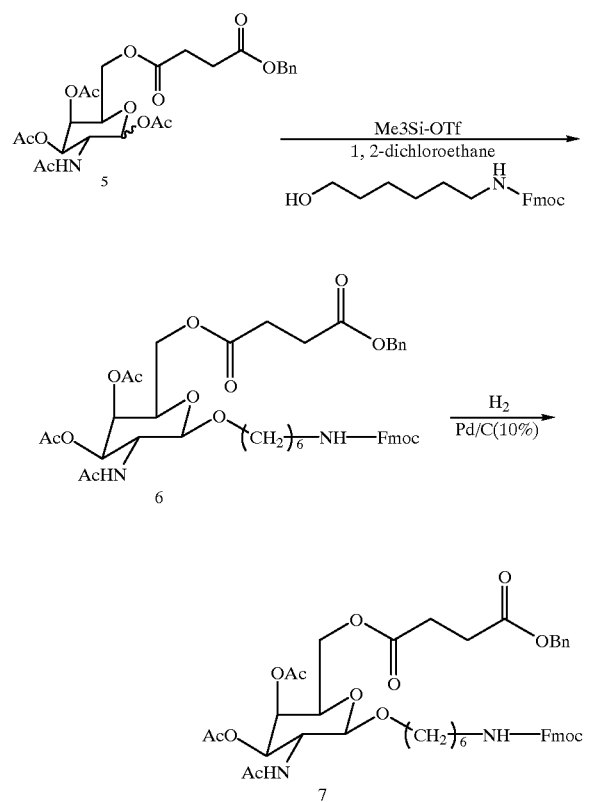

A solution of 5 (5.37 g, 10 mmole) and Fmoc protected 6-amino-1-hexanol (MW: 339, 6.78 g, 20 mmole) in dry 1,2-dichloroethane (ACROS, 50 mL) was stirred at 50° C. with 1.1 equiv of $Me_3Si$-triflate (ACROS, MW: 222.26, d: 1.15, 2.13 mL, 11 mmole). The mixture was stirred at 50° C. for 16 hr. The resulting solution was neutralized with triethylamine, concentrated in vacuo (water pump), and then applied to a column of silica gel (MERCK, Kieselgel 60; 70–230 mesh), eluted with $EA/CH_2Cl_2$ (1: 1.6) to give 6 (MW: 816, 6.36 g) with 78% yield as a foam.

A solution of 6 in methanol (100 mL) was shaken at a $H_2$ pressure of 4 bar in the presence of Pd/C (5%) (1.5 g) at room temperature for 3 hr. The residue was filtered through celite and washed with methanol. The combined filtrates were concentrated in vacuo (water pump), and then purified by flash chromatography [$EA/CH_2Cl_2/AcOH$ (3: 7: 0.1)] to give 7 (MW: 726, 5.1 g) with 90% yield as a foam.

Scheme 2:

Oxazoline was prepared from 2-acetoamide-1,3,4,6-tetra-O-acetyl-2-deoxy-D-glucopyranose according to *Carbohydrate Research* 150 (1986) C7-C1O. The amino acid derivative 8 was obtained by coupling 6-amino hexanol with γ-Fmoc-Glu(tBu).

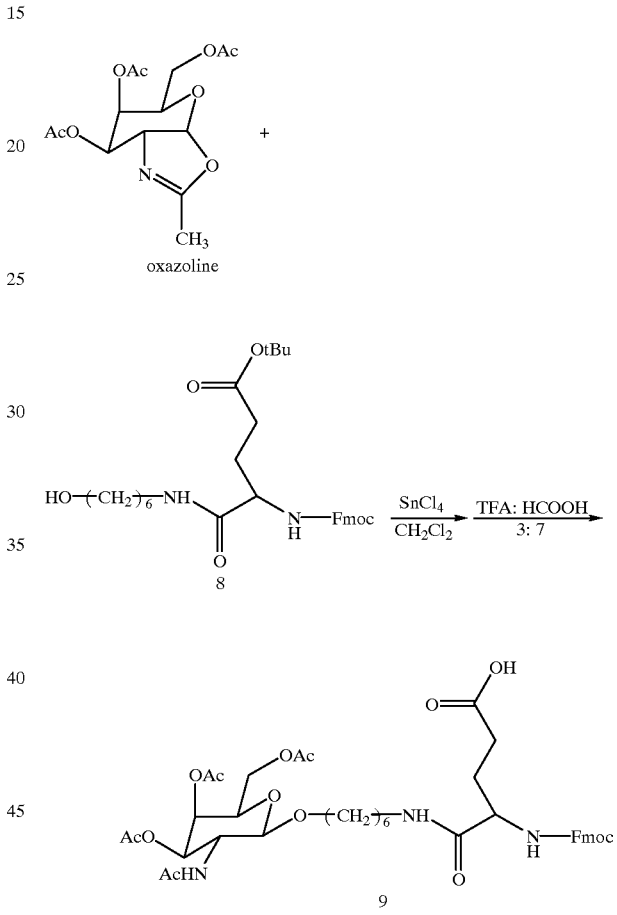

A solution of oxazoline (MW: 329, 3.29 g, 10 mmole) and 8 (MW: 524, 7.86 g, 15 mmole) in dry $CH_2Cl_2$ (ACROS, 50 mL) was added $SnCl_4$ (MW: 260.5, d: 2.226, 0.06ml, 0.5 mmole). The mixture was stirred at room temperature for over night, and then diluted with ethyl acetate (50 mL), washed with sat. $NaHCO_3$ solution (100 mL) and water (100 mL). The organic layer was dried ($MgSO_4$), and concentrated in vacuo (water pump). The residue was dissolved in HCOOH (35 mL)/TFA (15mL) solution, and stirred at room temperature for 2 hr. The resulting solution was concentrated in vacuo (Rotavapor connected to oil pump). The crude product was recrystallized by EA/ether to give 9 (MW: 797, 7.17 g) with 90% yield.

Scheme 3
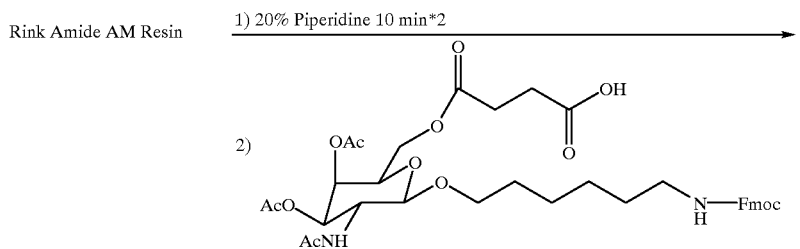
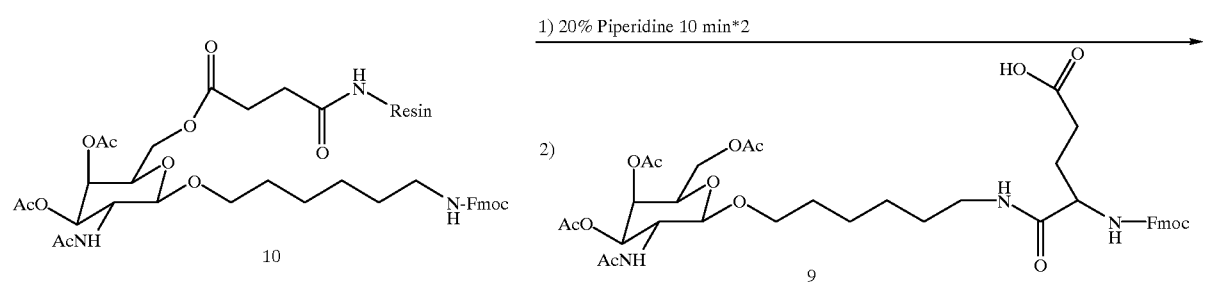
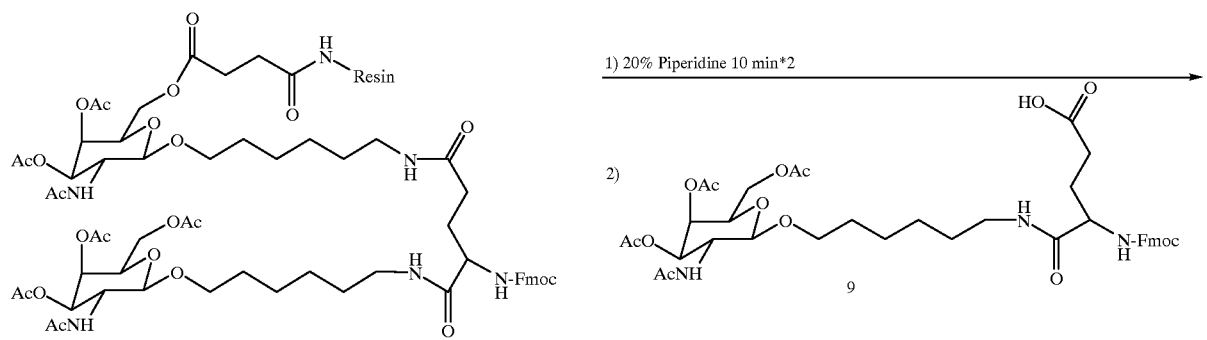

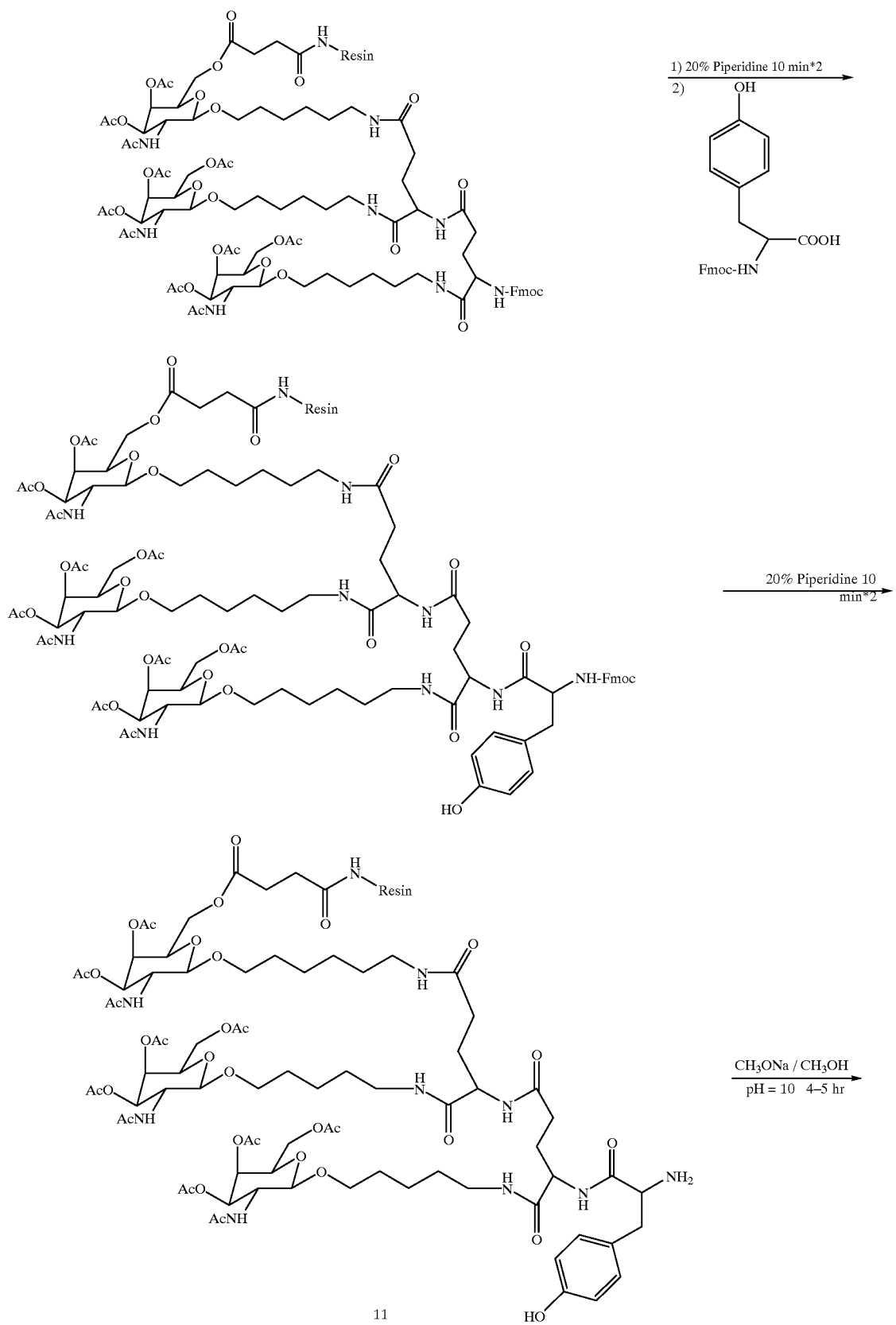

-continued

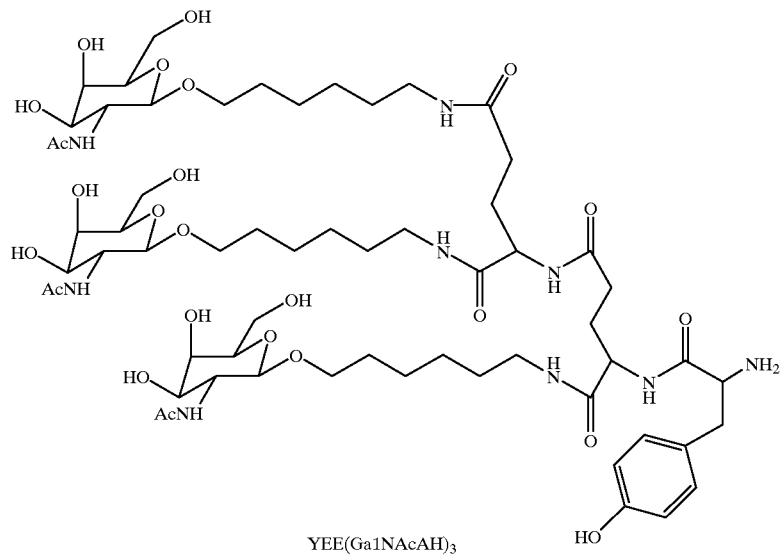

YEE(GalNAcAH)₃

Rink amide AM resin (Novabiochem, 0.66 mmole/g, 0.128 g, 0.084 mmole) was used as starting material. The resin was put into a glass reaction vessel, and then the solid phase synthesis was performed by using a standard FastMoc protocol on an automated peptide synthesizer (PS3, Rainin).

The Fmoc protecting group of Rink amide AM resin was removed by 5 mL 20% (v/v) piperidine (MERCK) at room temperature for 15 minutes two times. After disposing the piperidine solution, the resin was washed by N,N-dimethylformamide (DMF) (TEDIA, 5 mL) six times. 7 (0.244 g, 0.336 mmole) was activated by PYBOP (Novabiochem, MW: 520, 0.175 g, 0.336 mmole) in 5 mL 0.4M N-methylmorpholine (MERCK) DMF solution at room temperature for 30 seconds. In the coupling step, the activated 7 was reacted with Rink amide AM resin under $N_2$ at room temperature for 1 hr. Dispose excess 7, wash by DMF (5 mL) 3 times, and then the compound 10 was formed. Deprotecting and coupling steps were repeated with each subsequent amino acid derivative until 11 was completed.

11 was put into methanol (30 mL), and then sodium methoxide (ACROS) was added into solution until pH 10. The mixture was stirred at room temperature for 4 hr. The resulting solution was neutralized with acetic acid, filtered, and then the filtrates were concentrated in vacuo (oil pump). The crude product was purified by HPLC. Fractions containing YEE (GalNAcAH)₃ were collected, and the solvent was removed by lyophilization to give YEE (GalNAcAH)₃ (MW: 1346.5, 0.095 g) with 83% yield.

Scheme 4

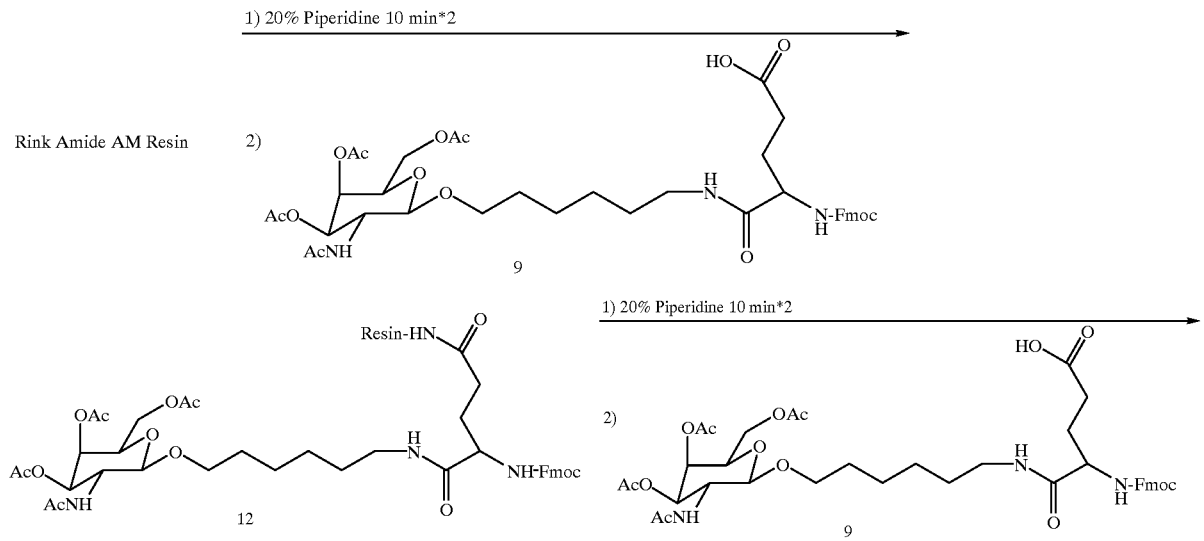

-continued
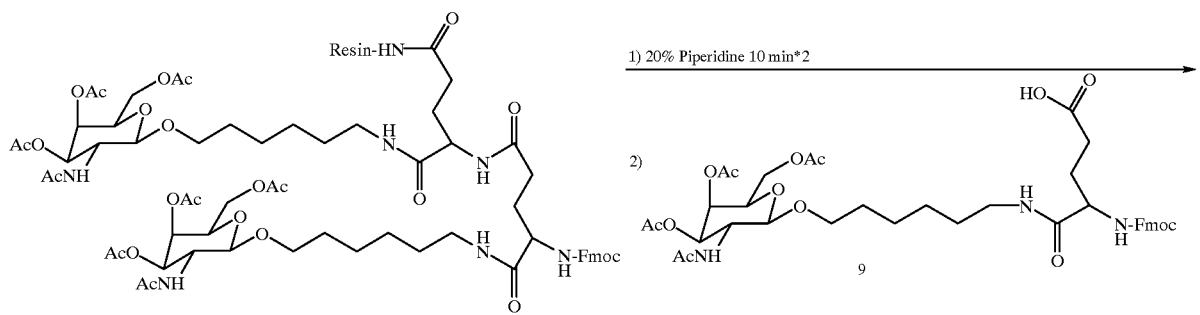
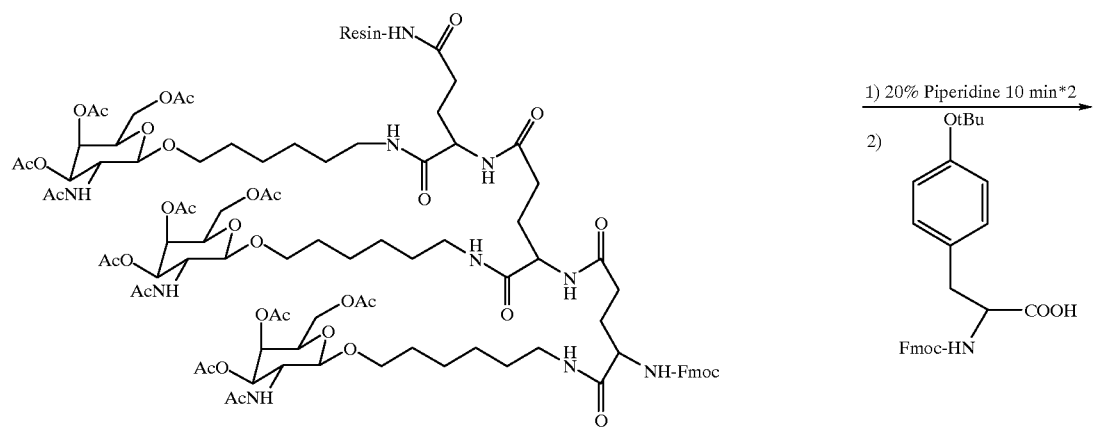
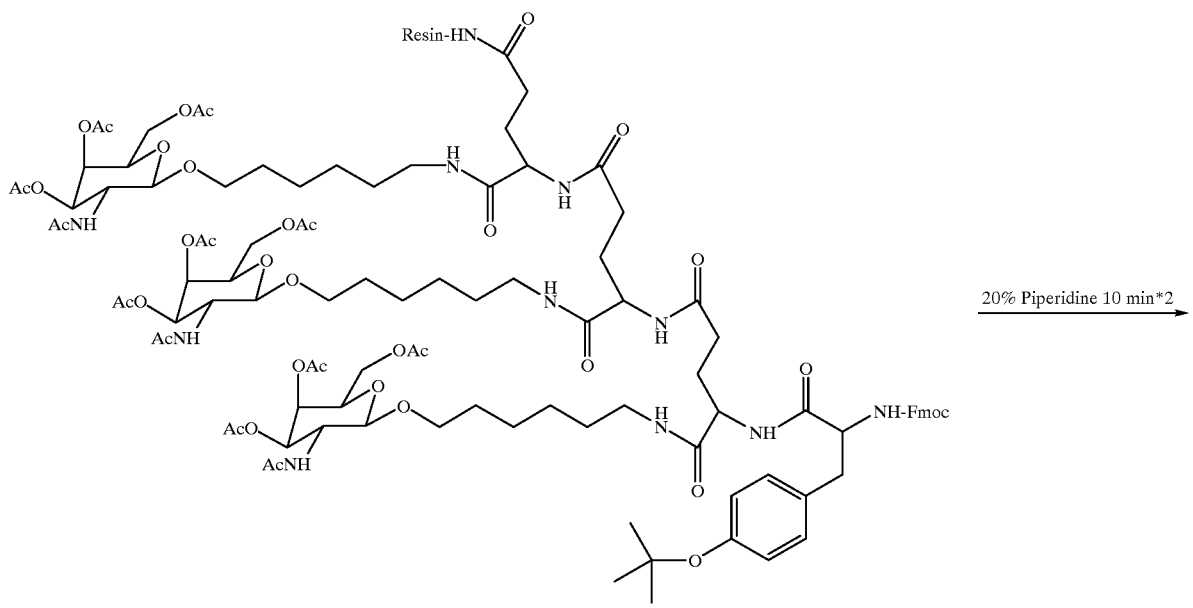

-continued
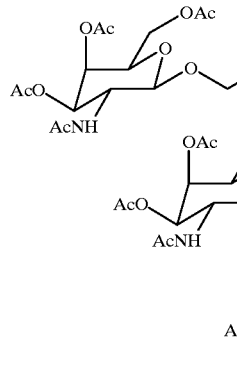
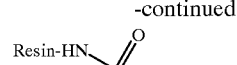
TFA:H₂O:EDT (95:2.5:2.5)
ice bath 1 hr
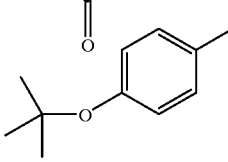
13
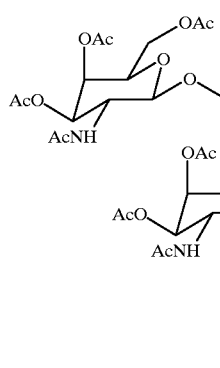
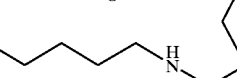
CH₃ONa / CH₃OH
pH = 10  4–5 hr
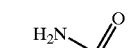
14
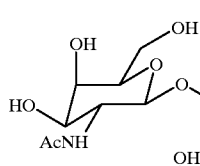
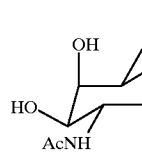
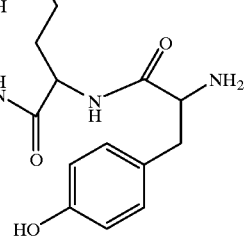
YEEE(GalNAcAH)₃

Rink amide AM resin (0.213 g, 0.141 mmole) was used as starting material. The resin was put into a glass reaction vessel, and then the solid phase synthesis was performed by using a standard FastMoc protocol on an automated peptide synthesizer (PS3, Rainin).

The Fmoc protecting group of Rink amide AM resin was removed by 5 mL 20% (v/v) piperidine (MERCK) at room temperature for 15 minutes two times. After disposing the piperidine solution, the resin was washed by DMF (5 mL) six times. 9 (0.418 g, 0.524 mmole) was activated by PyBOP (0.283 g, 0.524 mmole) in 5 ml 0.4M N-methylmorpholine DMF solution at room temperature for 30 seconds. In the coupling step, the activated 9 was reacted with Rink amide AM resin under $N_2$ at room temperature for 1 hr. Dispose excess 9, wash by DMF (5 mL) 3 times, and then the compound 12 was formed. Deprotecting and coupling steps were repeated with each subsequent amino acid derivative until 13 was completed.

13 was treated with 10 mL 1,2-ethanedithiol (Sigma)/$H_2O$/TFA (0.25: 0.25: 9.5) at 0° C. for 1.5 hr. The TFA and 1,2-ethanedithiol were removed in vacuo (oil pump) to give 14. 14 was dissolved into methanol (30 mL), and then sodium methoxide was added into solution until pH 10. The mixture was stirred at room temperature for 4 hr. The resulting solution was neutralized with acetic acid, and then concentrated in vacuo (oil pump). The crude product was purified by HPLC. Fractions containing YEEE (GalNAcAH)$_3$ were collected, and the solvent was removed by lyophilization to give YEEE(GalNAcAH)$_3$. (MW: 1474.7, 0.165 g) with 79% yield. Compounds oxazoline, 8, 9, 12, and YEEE(GalNAcAH)$_3$ were confirmed by mass analysis and NMR spectrum.

According to the above procedures, the synthesis of YEE and YEEE (SEQ ID NO: 1) has similar synthesis strategy. Both of these two compounds were synthesized by solid phase synthesis method. But YEE and YEEE (SEQ ID NO: 1) have some differences in starting material and cleavage steps. When synthesizing YEE, three amino acid derivatives were needed (compound 7, 9, and Fmoc-Tyr). When synthesizing YEEE (SEQ ID NO: 1), only two amino acid derivatives were needed (compound 9, and Fmoc-Tyr(tBu)). Although the synthesis of YEEE (SEQ ID NO: 1) need the use of TFA solution to cleave glycopeptide from the resin, we think that the synthesis of YEEE (SEQ ID NO: 1) is simpler and more economical because the starting material is easy to prepare. Both of these two synthetic methods are applicable to synthesizing other ligands. For example, Fmoc-Tyr can be replaced by other amino acid derivatives, the glutamic acid used in synthesis 9 can be replaced by aspartic acid, and the 6-amino-1-hexanol used in synthesis 7 or 9 can be replaced by other similar compounds.

We have experimentally confirm the binding specificity of YEEE(GalNAcAH)$_3$ to the human hepatoma cell, HepG2. HepG2 cells were grown in Dulbecco's modified Eagles medium (DMEM) with 10% fetal bovine serum. The cells were supplemented with 100 μg/ml streptomycin in an atmosphere containing 5% $CO_2$ at 37° C. For the experiment with fluorescein-labeled YEEE(GalNAcAH)$_3$, cells (1×10$^7$ ml) were incubated at 4° C. (for the binding study) or 37° C. (for the internalization study) for 1 hour with 100 μg/ml of the fluorescein-labeled YEEE(GalNAcAH)$_3$ in 1 ml PBS. Cells were then washed with PISS, suspended, fixed with 4% paraformaldehyde, and observed under a flurescence microscope (Nikon RFL).

Confocal microscopic observation showed that incubation of HepG2 cells with fluorescein-labeled YEEE (GalNAcAH)$_3$ at 4° C. resulted in a specific but diffusely distributed flurescence along the cell surface, whereas upon incubation at 37° C. under parallel conditions, denser fluorescent grains were visible in cell cytosol, suggesting that the cell surface-bound YEEE(GalNAcAH)$_3$ was internalized vis ASGP-r mediated endocytosis. In contrast, no binding of fluorescein-labeled YEEE(GalNAcAH)$_3$ (1 mg/ml) was found on the surface of CHO cells.

All references cited herein are hereby incorporated by reference.

As will be appreciated by those skilled in the art, various modifications, adaptations and variations of the foregoing specific disclosure can be made without departing from the teaching of the present invention.

The invention is not limited by the embodiments described above which are presented as examples only but can be modified in various ways within the scope of protection defined by the appended patent claims.

What is claimed is:

1. A method of synthesizing branched galactose-terminal glycoprotein comprising the steps of:

coupling an amino alcohol with a chemically protected ester of a dicarboxylic acid, which dicarboxylic acid is selected from the group consisting of glutamic and aspartic acids to produce A;

reacting A with the oxazoline of N-acetyl galactosamine to produce the amino acid derivative B;

reacting a 1,3 diacetate of N-acetyl galatosamine with a monobenzyl ester of a dicarboxylic acid selected from the group consisting of succinic, glutaric, adipic, maleic and fumaric acids to produce C;

reacting C with a chemically protected amino alkyl alcohol to produce D;

attaching D to an amide resin;

reacting the attached D with B to form E that is attached to the amide resin;

reacting the attached E with an amino acid having a chemically protected amino group;

deprotecting and cleaving from the resin to form the branched galactose-terminal glycoprotein.

2. The method of claim 1 wherein the amino alcohol is 6-amino hexanol.

3. The method of claim 1 wherein the chemically protected ester of a dicarboxylic acid is γ-Fmoc-Glu(tBu).

4. The method of claim 1 wherein the chemically protected ester of a dicarboxylic acid is γ-Fmoc-Asp(tBu).

5. The method of claim 1 wherein the monobenzyl ester of a dicarboxylic acid is succinic acid monobenzyl ester.

6. The method of claim 1 wherein the attached E is reacted with tyrosine having a chemically protected amino group.

7. The method of claim 1 wherein the chemically protected ester of a dicarboxylic acid is γ-Fmoc-Glu(tBu) and the monobenzyl ester of a dicarboxylic acid is the monobenzyl ester of succinic acid.

8. The method of claim 7 wherein E has at least two galactose terminal groups.

9. The method of claim 7 wherein E has at least three galactose terminal groups.

10. The method of claim 9 wherein the branched galactose-terminal glycoprotein is YEE(GalNAcAH)$_3$.

11. A method of synthesizing branched galactose-terminal glycoprotein comprising the steps of:

coupling an amino alcohol with a chemically protected ester of a dicarboxylic acid, which dicarboxylic acid is selected from the group consisting of glutamic and aspartic acids, to produce A;

reacting A with the oxazoline of the N-acetyl galactosamine to produce the amino acid derivative B;

attaching B to an amide resin;

reacting the attached B with unattached B to form C that is attached to the amide resin;

reacting the attached C with an amino acid having a chemically protected amino group; deprotecting and cleaving from the resin to form the branched galactose-terminal glycoprotein.

12. The method of claim 11 wherein the amino alcohol is 6-amino hexanol.

13. The method of claim 11 wherein the chemically protected ester of a dicarboxylic acid is γ-Fmoc-Glu(tBu).

14. The method of claim 11 wherein the chemically protected ester of a dicarboxylic acid is γ-Fmoc-Asp(tBu).

15. The method of claim 11 wherein the attached C is reacted with tyrosine having a chemically protected amino group.

16. The method of claim 11 wherein C has at least two galactose terminal groups.

17. The method of claim 11 wherein C has at least three galactose terminal groups.

18. The method of claim 17 wherein the branched galactose-terminal glycoprotein is YEEE(GalNAcAH)$_3$.

19. A branched galactose-terminal glycoprotein having binding affinity to the asialoglycoprotein receptor produced by the process of claim 11.

20. The branched galactose-terminal glycoprotein of claim 19, having three galactose terminal groups.

21. The branched galactose terminal glycoprotein having the following chemical structure:

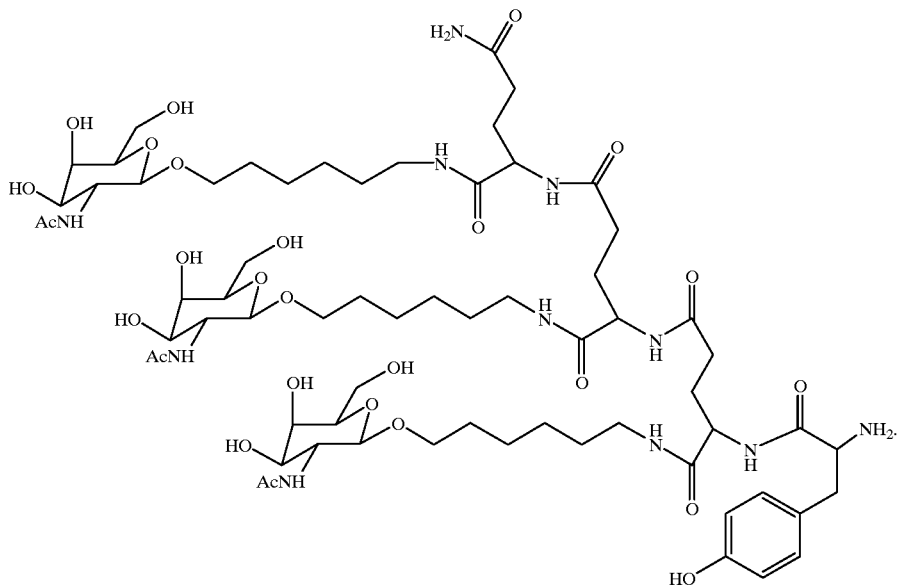

22. A conjugate having a branched galatose-terminal glycoprotein having the chemical structure according to claim 21, which is complexed to a therapeutically effective agent.

23. The conjugate of claim 22, wherein the therapeutically effective agent is selected from the group consisting of a nucleic acid, protein, polysaccharide, lipid and radioactive isotope.

24. The conjugate of claim 23, wherein the nucleic acid is DNA.

25. The conjugate of claim 23, wherein the nucleic acid is RNA.

26. The conjugate of claim 23, wherein the protein is interferon.

27. A method of delivering a therapeutically effective agent to a mammalian cell comprising administering to a mammal a conjugate having a branched galatose-terminal glycoprotein having the chemical structure according to claim 21, which is complexed to a therapeutically effective agent.

28. A method of transfecting hepatocytes comprising adding to the hepatocytes a composition comprising a complex comprising an isolated nucleic acid and a branched galatose-terminal glycoprotein having the chemical structure according to claim 21.

29. The method of claim 28, wherein the isolated nucleic acid is DNA.

30. The method of claim 29, wherein the isolated nucleic acid comprises sequences of antisense oligonucleotides of PKC (protein kinase C) α: having a sequence of (5'-3') CAGCCATGGTTCCCCCCAAC (SEQ ID NO: 2).

* * * * *